United States Patent [19]

Halczenko et al.

[11] Patent Number: 4,599,341

[45] Date of Patent: Jul. 8, 1986

[54] SUBSTITUTED AND BRIDGED PYRIDINES USEFUL AS CALCIUM CHANNEL BLOCKERS

[75] Inventors: Wasyl Halczenko, Hatfield; George D. Hartman, Lansdale, both of Pa.

[73] Assignee: Merck & Co., Inc., Rahway, N.J.

[21] Appl. No.: 655,778

[22] Filed: Oct. 1, 1984

[51] Int. Cl.$^4$ .................. A61K 31/44; A61K 31/47; C07D 491/08
[52] U.S. Cl. .............................. 514/282; 546/43; 546/44; 546/39; 546/40; 546/63; 546/34; 544/61; 544/125; 544/361; 514/222; 514/236; 514/253; 514/279; 514/281; 514/286
[58] Field of Search .................. 546/43, 44, 39, 40, 546/74, 63; 544/61, 125, 361; 514/222, 236, 253, 281, 282, 289, 279, 280, 284

[56] References Cited

U.S. PATENT DOCUMENTS

| | | | |
|---|---|---|---|
| 3,466,288 | 9/1969 | Hansen et al. | 546/74 X |
| 3,518,271 | 6/1970 | Shavel, Jr. et al. | 546/43 |
| 4,172,201 | 10/1979 | Jarque et al. | 546/63 |
| 4,178,450 | 12/1979 | Jarque et al. | 546/63 |

OTHER PUBLICATIONS

Bossert et al., Angew. Chem. Int. Ed., vol. 20, pp. 762–769 (1981).
Schramm et al., Nature, vol. 309, pp. 535–537, (Jun. 9, 1983).

*Primary Examiner*—Donald G. Daus
*Assistant Examiner*—Diana G. Rivers
*Attorney, Agent, or Firm*—Alice O. Robertson; Joseph F. DiPrima; Michael C. Sudol

[57] ABSTRACT

Novel substituted and bridged pyridine compounds useful as calcium channel blockers, pharmaceutical compositions thereof, and methods of treatment are disclosed.

9 Claims, No Drawings

SUBSTITUTED AND BRIDGED PYRIDINES USEFUL AS CALCIUM CHANNEL BLOCKERS

BACKGROUND OF THE INVENTION

Substituted dihydropyridines are known to be useful for reducing blood pressure, effecting dilation of the coronary vessels, and preventing urospasms. Typical of such substituted dihydropyridines are those disclosed in U.S. Pat. Nos. 3,923,818; 3,905,970; 4,044,141; 4,237,137; and 4,285,955. The substituted dihydropyridines disclosed in these patents do not include bridged ring structures.

Weller et al., [J. Org. Chem., 48, pp 3061-7 (1983)] disclose 1'-methylspiro[benzofuran-3(2H), 4'-piperdine] as a substructure of morphine which is an early intermediate in a general synthesis of morphine but not possessing exceptional analgesic activity. Weller et al. also teach the preparation of spiro [benzofuran-3(2H), 4'-(1'H)-pyridines] as potential intermediates in a synthesis of morphine but no biological activity of these compounds is reported.

Goldman [Angew. Chem. Int. Ed. Engl., 20, pp. 779-780 (1981)] teaches the preparation of spiro[benzothiophene-1-oxide, 4'-pyridines] as an intermediate in the preparation of 4,4-disubstituted 1,4-dihydropyridines.

SUMMARY OF THE INVENTION

This invention is directed to novel substituted and bridged pyridines and derivatives thereof and to methods for preparing such compounds. This invention is also directed to pharmaceutical compositions and methods of treatment for cardiovascular disorders in which high cellular concentration of $Ca^{++}$ is a factor.

DETAILED DESCRIPTION OF THE INVENTION

The specific substituted and bridged pyridine compounds of this invention are represented by the following general structural formulae (I) and (II):

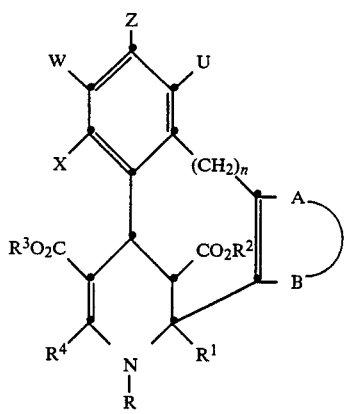
(I)

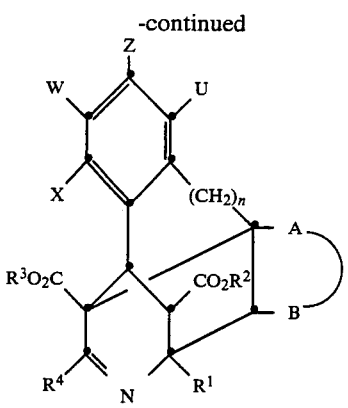
(II)

wherein:
n is 0, 1, or 2;
A is oxygen, sulfur or $>NR^9$ in which $R^9$ is hydrogen or $C_1-C_4$ alkyl, and
B is —CH=CH— or

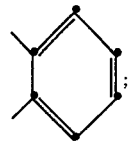;

or

B is oxygen, sulfur or $>NR^9$, and A is —CH=CH— or

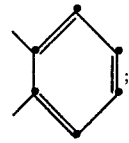;

and
R is hydrogen or $C_1-C_8$ alkyl;
$R^1$ and $R^4$ independently are hydrogen, $C_1-C_8$ alkyl, $C_2-C_8$ alkenyl, $C_3-C_8$ cycloalkyl or $C_1-C_8$ hydroxyalkyl;
$R^2$ and $R^3$ independently are $C_1-C_8$ alkyl, $C_2-C_8$ alkenyl, $C_3-C_8$ cycloalkyl, $C_1-C_8$ hydroxyalkyl, $C_1-C_8$ dihydroxyalkyl, $C_2-C_8$ alkoxyalkyl, $C_3-C_8$ alkoxy(alkoxyalkyl) or $C_1-C_8$ aminoalkyl wherein the amino group is $NR^5R^6$ in which $R^5$ and $R^6$ independently are hydrogen, $C_1-C_8$ alkyl, $C_7-C_{14}$ phenylalkyl or $R^5$ and $R^6$ together with the N atom form a 5 or 6 membered heterocycle selected from the group consisting of piperidinyl, morpholinyl, thiomorpholinyl, pyrrolidinyl, piperazinyl or $N'-C_1-C_4$-alkylpiperazinyl; and
X, W, Z and U independently are hydrogen, $C_1-C_8$ alkyl, $C_1-C_8$ alkoxy, $CF_3$, cyano, nitro or halo, (i.e. fluoro, chloro or bromo) provided that at least two of X, W, Z and U are hydrogen or X and W or W and Z or Z and U together with the phenyl group to which they are attached form a naphthyl or benzoxadiazole group,
and pharmaceutically acceptable salts thereof.

The preferred compounds of this invention are those represented by the general structural formulae (I) and (II) wherein:
n is 0 or 1;

A is oxygen or sulfur and B is —CH═CH—; or
B is oxygen or sulfur and A is —CH═CH—; and
R is hydrogen;

$R^1$ and $R^4$ independently are hydrogen or $C_1$-$C_8$ alkyl;

$R^2$ and $R^3$ independently are $C_1$-$C_8$ alkyl or $C_1$-$C_8$ aminoalkyl wherein the amino group is $NR^7R^8$ in which $R^7$ and $R^8$ independently are hydrogen, $C_1$-$C_8$ alkyl or $C_7$-$C_{14}$ phenylalkyl; and X, W, Z and U independently are hydrogen, $C_1$-$C_8$ alkoxy, $CF_3$, cyano, nitro or halo provided that at least two of X, W, Z and U are hydrogen.

The most preferred compounds of this invention are those preferred compounds wherein: $R^1$, $R^2$, $R^3$ and $R^4$ independently are $C_1$-$C_8$ alkyl and X, W, Z and U are hydrogen.

The compounds of this invention possess asymmetric centers and thus exist in different isomeric forms. All such forms are included within the scope of this invention. Specifically, the compounds have an asymmetric center at the carbon atom to which the ester moiety, —$CO_2R^2$, is attached. Whenever that ester moiety is below the plane of the piperidine ring (i.e. down) that stereochemical configuration is denoted as the alpha (α)-isomer. Similarly, whenever that ester moiety is above the plane of the piperidine ring (i.e. up) that stereochemical configuration is denoted as the beta (β)-isomer.

Illustrative of the compounds of this invention are the following compounds of the formulae (I) and (II) which are the α-isomer, the β-isomer or mixtures thereof:

(1) Dimethyl 5,8-dihydro-4,6-dimethyl-4,8-methano-4H-thieno[2,3-a][4]benzazocine-7,13β dicarboxylate [Formula (I) where n is 0, A is sulfur, B is —CH═CH—, R is hydrogen, $R^1$, $R^2$, $R^3$ and $R^4$ are methyl and X, W, Z and U are hydrogen];

(2) Dimethyl 3a,4,6a,7-tetrahydro-4,6-dimethyl-4,8-methanoindeno[2,1-c]thieno[2,3-d]pyridine-6a,12β-dicarboxylate [Formula (II) where n is 0, A is sulfur, B is —CH═CH—, $R^1$, $R^2$, $R^3$ and $R^4$ are methyl and X, W, Z and U are hydrogen];

(3) Dimethyl 5,8-dihydro-4,6-dimethyl-4,8-methano-4A-thieno[3,2-a][4]benzazocine-7,13β-dicarboxylate [Formula (I) where n is 0, A is —CH═CH—, B is sulfur, R is hydrogen, $R^1$, $R^2$, $R^3$ and $R^4$ are methyl and X, W, Z and U are hydrogen]; and (4) Dimethyl 4,6a,7,12-tetrahydro-4,6-dimethyl-4,7-methano-3aH-benzo[g]furo[2,3-d]isoquinoline-6a,13β-dicarboxylate [Formula (II) where n is 1, A is —CH═CH—, B is oxygen, $R^1$, $R^2$, $R^3$ and $R^4$ are methyl and X, W, Z and U are hydrogen].

The pharmaceutically acceptable salts are those acid addition salts of non-toxic, pharmaceutically acceptable acids and include salts of inorganic acids such as hydrochloric, hydrobromic, hydroiodic, phosphoric, sulfuric, nitric and the like, and organic acids such as trifluoroacetic, and trichloroacetic, acetic and the like and include acids related to the pharmaceutically acceptable salts listed in Journal of Pharmaceutical Science, 66, 2 (1977) and incorporated herein by reference.

The compounds of this invention are conveniently prepared from known or readily obtainable starting materials utilizing the general synthetic pathway described below:

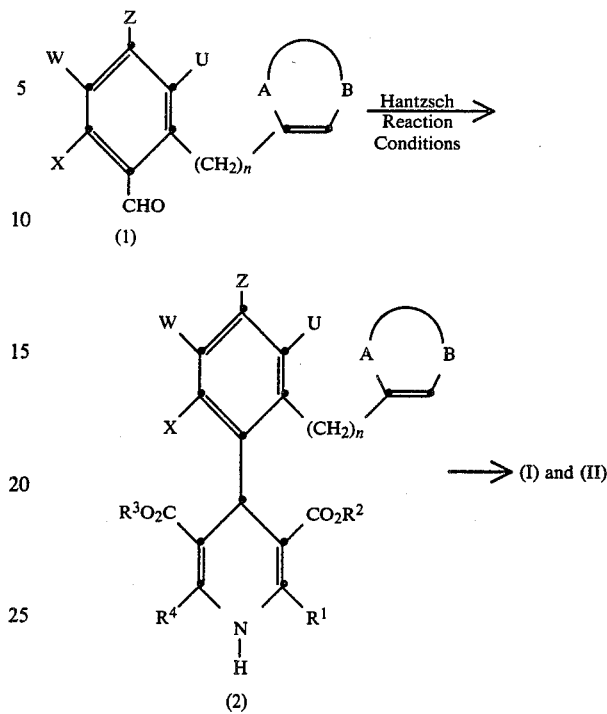

The aryl aldehyde (1), wherein n, A, B, X, W, Z and U are described above, is reacted with an appropriately substituted 3-aminopropenoate, such as methyl 3-aminocrotonate, and an appropriately substituted 3-oxopropanoate, such as methyl acetoacetate, under the general Hantzsch reaction conditions to afford the aryl dihydropyridine compound (2).

The aryl dihydropyridine compound (2) is then treated at −10° to 50° C., preferably at ambient temperature, with between 0.5 and 5.0 equivalent, preferrably 1.0 equivalent, of a Lewis acid in an inert solvent to yield the compound of formula (I). Examples of such Lewis acids include aluminum chloride, titanium tetrachloride, trimethylsilyl trifluoromethanesulfonate and tin tetrachloride. Exemplifying the inert solvents employed in this cyclization reaction are ethers, chlorinated hydrocarbons and aromatic hydrocarbons. The preferred solvents are methylene chloride, chloroform and benzene.

As indicated above, the compounds of this invention are useful as calcium channel blockers, and thus have broad pharmacological utility in that they exhibit (i) pronounced and long-lasting vasodilating effect accompanied by an energy-sparing effect on cardiac metabolism; (ii) antiarrythmic and antianginal action on cardiac muscle; (iii) vascular spasmolytic action; (iv) antihypertensive action; (v) spasmolytic action on the smooth muscle of the gastrointestinal and urogenital tracts and the cerebrovascular and respiratory system; (vi) useful antihypercholesterolemic and antilipademic action; (vii) protection of the ischemic myocardium; (viii) inhibition of irritable bowel syndrome and esophageal spasm; and, (ix) inhibition of migraine. Some of these compounds are also useful cardiotonic agents.

The representative compounds of the present invention were found to inhibit vascular calcium contraction, reduce cardiac contractile force, inhibit calcium-mediated tracheal contraction, inhibit calcium uptake in pituitary cells, or displace triturated nitrendipine from membrane.

The compounds of the present invention can be administered in any suitable form; e.g. orally, sublingually, transdermally, or parenterally; i.e. intravenously, interperitoneally, etc. Thus, the compounds can be offered in a form (a) for oral administration e.q. as tablets in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for sublingual administration; e.g., nitroglycerine tablets, lactose tablets, and the like, for rapid dissolution or high molecular weight methylcellulose tablets, carboxymethylcellulose tablets, and the like, for slower, time-releasing delivery; or, (c) for parenteral administration e.g. dissolved or dispersed in a suitable liquid carrier or emulsified.

The pharmaceutical preparations thus described are made following the conventional techniques of the pharmaceutical chemist as appropriate to the desired end product.

The ratio of active compound to compounding ingredients i.e. carrier, diluent etc. will vary as the dosage form requires. Whatever form is used, the amount of compound of the present invention administered should be sufficient to achieve the pharmaceutical and/or therapeutic effect desired or required in the patient. Generally, doses of the compounds of the invention of from about 30 to about 3000 mg per day may be used, preferably about 100 to about 1000 mg per day. Dosages may be single or multiple depending on the daily total required and the unit dosage administered. Of course, the dose will vary depending upon the nature and severity of disease, weight of the patient, and other factors which a person skilled in the art will recognize.

It is often advantageous to administer compounds of this invention in combination with angiotensin converting enzyme inhibitors and/or antihypertensives and/or diuretics and/or β-blocking agents. For example, the compounds of this invention can be given in combination with such compounds as enalapril, hydralazine hydrochloride, hyrochlorothiazide, methyldopa, timolol, and the like, as well as admixtures and combinations thereof.

Typically, the individual daily dosages for these combinations can range from about one-fifth of the minimally recommended clinical dosages to the maximum recommended levels for the entities when they are given singly. Naturally, these dose ranges can be adjusted on a unit basis as necessary to permit divided daily dosages and, as noted above, can be varied depending on the nature and severity of the disease, weight of patient, special diets and other factors.

The following Examples are provided to further illustrate the best mode currently known for preparing the compounds and compositions of this invention, but are not to be construed as limiting this invention in any manner.

EXAMPLE 1

Preparation of Dimethyl 5,8-dihydro-4,6-dimethyl-4,8-methano-4H-thieno[2,3-a][4]benzazocine-7,13β-dicarboxylate and Dimethyl 3a,4,6a,7-tetrahydro-4,6-dimethyl-4,8-methanoindeno[2,1-c]thieno[2,3-d]pyridine-6a,12β-dicarboxylate (a) 2-(2-Thienyl)benzaldehyde (1a)

To a solution of 3-bromothiophene (30 mmol) in tetrahydrofuran (20 mL) at $-78°$ C. under nitrogen was added dropwise n-butyllithium in hexane (30 mmol). The mixture was stirred for 45 minutes and magnesium bromide etherate (45 mmol) was added portionwise. The reaction mixture was then allowed to warm to $-20°$ C. over 45 minutes. This mixture was added to a suspension of di-μ-acetato-bis[2-(N-phenylformimidoyl)phenyl]dipalladium (15 mmol) [Onoue et al., *J. Organometallic Chem.*, 43, pp. 431–436 (1972)] and triphenylphosphine (60 mmol) in benzene (250 mL) and the reaction mixture stirred at ambient temperature overnight. The cooled reaction mixture was quenched with 1N hydrochloric acid (175 mL), was stirred for 2.5 hours, filtered, and the phases separated. The aqueous phase was extracted with diethyl ether (2×150 mL) and the combined organic phases were washed with brine and dried over anhydrous sodium sulfate. After filtration, the solvent was removed in vacuo to give an oil which was purified by flash chromatography on silica gel eluted with ethyl acetate:hexane (3:97) to yield Compound 1a as an oil ($R_f$=0.4).

(b) Dimethyl 2,6-dimethyl-4-[2-(2-thienyl)phenyl]-1,4-dihydropyridine-3,5-dicarboxylate (1b)

To a solution of Compound 1a (0.5 mmol) in methanol (5 mL) was added methyl acetoacetate (1.0 mmol) and concentrated ammonium hydroxide (1.0 mmol) and the reaction mixture was refluxed for 4 days. The solvent was removed in vacuo and the residue purified by flash chromatography on silica gel eluted with diethyl ether:hexane (1:1) and trituration with diethyl ether:hexane (1:2) to afford Compound 1b as a white solid (m.p. 173°–175° C.).

(c) Dimethyl 5,8-dihydro-4,6-dimethyl-4,8-methano-4H-thieno[2,3-a][4]benzazocine-7,13β-dicarboxylate (1A) and Dimethyl 3a,4,6a,7-tetrahydro-4,6-dimethyl-4,8-methanoindeno[2,1-c]thieno[2,3-d]pyridine-6a,12β-dicarboxylate (1B)

To a solution of Compound 1b (0.8 mmol) in chloroform (20 mL) at ambient temperature under nitrogen was added aluminum chloride (1.0 mmol) and the resulting suspension was stirred overnight. The cooled reaction mixture was quenched in water (20 mL), made basic with saturated aqueous sodium bicarbonate and diluted with chloroform (100 mL). The organic phase was separated, washed with brine and dried over anhydrous sodium sulfate. The solvent was removed in vacuo and the residue was purified by flash chromatography on silica gel eluted with diethyl ether:hexane (2:1) to give Compound 1A ($R_f$=0.4, m.p. 185°–193° C.) and Compound 1B ($R_f$=0.3, m.p. 167°–173° C.).

EXAMPLE 2

Preparation of Dimethyl 5,8-dihydro-4,6-dimethyl-4,8-methano-4H-thieno[3,2-a][4]benzazocine-7,13β-dicarboxylate (a) 2-(3-Thienyl)toluene (2a)

To a solution of 2-bromotoluene (11.7 mmol) in tetrahydrofuran (25 mL) at $-78°$ C. under nitrogen was added n-butyllithium in hexane (11.7 mmol) and the resulting yellow suspension stirred for 45 minutes at −78° C. To this suspension at −78° C. was added magnesium bromide etherate (11.5 mmol) and after stirring for 15 minutes at −70° C., the reaction mixture was allowed to warm to ambient temperature over 45 minutes. The resultant solution was added at ambient temperature to a suspension of 3-bromothiophene (11.0 mmol) and bis(1,2-diphenylphosphino)ethane nickel (II) chloride (0.05 mmol) in diethyl ether (25 mL) that has been stirred for 15 minutes. The reaction mixture was heated at reflux for 16 hours and then cooled in an ice bath. To the cooled reaction mixture was added dilute hydrochloric acid (20 mL) and then diethyl ether (50 mL). The organic phase was washed with saturated aqueous sodium bicarbonate, brine and dried over anhydrous sodium sulfate. The solvent was removed in vacuo and the residue fractionated to give Compound 2a as a clear oil (b.p. 110°–114° C./7 mm).

(b) 2-(3-Thienyl)-α-bromotoluene (2b)

To a solution of Compound 2a (7.23 mmol) in carbon tetrachloride (150 mL) was added N-bromosuccinimide (7.5 mmol) and benzoyl peroxide (0.1 g). The solution was heated at reflux and irradiated with 250 watt sunlamp for 2 hours. The cooled reaction mixture was filtered through a pad of silica gel and the silica gel washed with diethyl ether (3×75 mL). The solvent was removed in vacuo and the residue fractionated to afford Compound 2b as a clear oil (b.p. 100°–103° C./0.1 mm).

(c) 2-(3-Thienyl)benzaldehyde (2c)

To a solution of Compound 2b (1.98 mmol) in chloroform (5 mL) was added pyridine (9.88 mmol) and the reaction mixture heated at reflux for 1 hour under nitrogen. The solvent was removed in vacuo and the residue triturated with diethyl ether to give a white solid. The solid was dissolved in 95% aqueous ethanol (10 mL ) and N,N-dimethyl-4-nitrosoaniline (1.98 mmol) was added with stirring followed by the addition of sodium hydroxide (4.0 mmol) in water (3 mL). The reaction mixture was stirred for 16 hours at ambient temperature and then 6N hydrochloric acid (3 mL) was added. After 30 minutes, the solvent was removed in vacuo and the residue was diluted with water (10 mL) and extracted with diethyl ether (2×30 mL). The combined organic phases were washed with saturated aqueous sodium bicarbonate, brine and the solvent removed in vacuo to give crude Compound 2c as an oil.

(d) Dimethyl 2,6-dimethyl-4-[2-(3-thienyl)phenyl]-1,4-dihydropyridine-3,5-dicarboxylate (2d)

To a solution of crude Compound 2c (10.6 mmol) in methanol (10 mL) was added methyl acetoacetate (10.6 mmol), methyl 3-aminocrotonate (10.6 mmol) and concentrated ammonium hydroxide (1 drop). The reaction mixture was heated at reflux under nitrogen for 4 days. The solvent was removed in vacuo and the residue purified by flash chromatography on silica gel eluted with diethyl ether:hexane (2:1) and trituration with diethyl ether:hexane (1:2) to yield Compound 2d as a pale yellow solid (m.p. 164°–166° C.).

(e) Dimethyl 5,8-dihydro-4,6-dimethyl-4,8-methano-4H-thieno[3,2-a][4]benzazocine-7,13β-dicarboxylate To a solution of Compound 2d (0.83 mmol) in chloroform (20 mL) was added aluminum chloride (1.0 mmol). After stirring for 24 hours at ambient temperature under nitrogen, the reaction was quenched with water and then neutralized with saturated aqueous sodium bicarbonate. The reaction mixture was extracted with methylene chloride (3×25 mL) and the combined organic phase was washed with brine and dried over anhydrous sodium sulfate. The solvent was removed in vacuo and the residue purified by flash chromatography on silica gel eluted with diethyl ether:hexane (1:1) to give the desired compound as the hemi-hydrate (m.p. 223°–233° C.).

EXAMPLE 3

Preparation of Dimethyl 4,6a,7,12-tetrahydro-4,6-dimethyl-4,7-methano-3a H-benzo[g]furo[2,3-d]isoquinoline-6a,13β-dicarboxylate (a) 2-Bromo-α-(3-thienyl)benzylalcohol (3a)

To a solution of n-butyllithium in hexane (2.7 mmol) and diethyl ether (2.5 mL) at −78° C. under nitrogen was added dropwise a solution of 3-bromofuran (3.0 mmol) in diethyl ether (1 mL). After stirring for 45 minutes at −78° C., to the reaction mixture was added dropwise 2-bromobenzaldehyde (2.7 mmol) in diethyl ether (1 mL). The reaction mixture was allowed to warm to ambient temperature and stirred for about 16 hours. The reaction was quenched with saturated aqueous ammonium chloride (1 mL), diluted with water (2 mL) and extracted with diethyl ether (3×10 mL). The combined organic phases were washed with water, and dried over anhydrous sodium sulfate. The solvent was removed in vacuo and the residue purified by flash chromatography on silica gel eluted with ethyl acetate:hexane (1:9) to yield Compound 3a as an oil ($R_f$=0.4).

(b) 2-(3-Furanylmethyl)bromobenzene (3b)

Aluminum chloride (78.0 mmol) dissolved in diethyl ether (40 mL) under nitrogen was added to a suspension of lithium aluminum hydride (78.0 mmol) in diethyl ether (40 mL) under nitrogen at 0° C. To the reaction mixture was added a solution of Compound 3a (52.0 mmol) in diethyl ether (25 mL) at such a rate that reflux was maintained. After an additional 15 minutes at reflux, the reaction mixture was cooled to 0° C. and dilute 3M sulfuric acid was added dropwise until the evolution of gas stopped. The reaction mixture was then poured onto ice (100 mL) and 3N hydrochloric acid (25 mL) and then extracted with diethyl ether (2×50 mL). The combined organic phases were washed with 3N hydrochloric acid, saturated aqueous sodium bicarbonate, water and brine and then dried over anhydrous sodium sulfate. The solvent was removed in vacuo and the residue purified by flash chromatography on silica gel eluted with ethyl acetate:hexane (2:98) to afford Compound 3b as an oil ($R_f$=0.4).

(c) 2-(3-Furanylmethyl)benzaldehyde (3c)

To a solution of Compound 3b (0.5 mmol) in tetrahydrofuran (2 mL) at −78° C. under nitrogen was added n-butyllithium in hexane (0.5 mmol). After 30 minutes, a solution of N- formylpiperidine (0.55 mmol) in tetrahydrofuran (0.5 mL) was added dropwise at −78° C. The reaction mixture was stirred for 5 hours while allowing it to warm to −10° C. The reaction was quenched with saturated aqueous ammonium chloride (1 mL) and diluted with diethyl ether (10 mL). The aqueous phase was extracted with diethyl ether (2×10 mL) and the combined organic phases were washed with saturated aqueous ammonium chloride (3×5 mL) and brine and then dried over anhydrous sodium sulfate. The solvent was removed in vacuo and the residue purified by flash chromatography on silica gel eluted with ethyl acetate:hexane (2:98) to afford Compound 3c as an oil ($R_f$=0.2).

(d) Dimethyl 2,6-dimethyl-4-[2-(3-furanylmethyl)]-phenyl-1,4-dihydropyridine-3,5-dicarboxylate (3d)

To a solution of Compound 3c (1.0 mmol) in methanol (2 mL) was added methyl acetoacetate (2.2 mmol) and concentrated ammonium hydroxide (2.2 mmol). Additional ammonium hydroxide (2 drops) was added and the reaction mixture heated to reflux for 3 hours. The solvent was removed in vacuo and the residue purified by flash chromatography on silica gel eluted with methanol:chloroform (1:99) to yield Compound 3d as a solid (m.p. 140°–143° C.).

sodium sulfate. The solvent was removed in vacuo and the residue purified by flash chromatography on silica gel eluted with methanol:chloroform (1:99) to give the desired product as a solid (m.p. 128°–131° C.).

EXAMPLES 4–20

Utilizing the general procedure of Examples 1, 2 or 3 and starting with appropriately substituted aryl aldehydes the following compounds of the formulae (I) and (II) wherein B is —CH=CH— and R is hydrogen are prepared.

| Compound | n | A | $R^1$ | $R^2$ | $R^3$ | $R^4$ | X | W | Z | U |
|---|---|---|---|---|---|---|---|---|---|---|
| 4 | 0 | O | Me | Et | Et | Me | H | H | H | H |
| 5 | 0 | S | Et | Et | Et | Et | H | H | H | H |
| 6 | 0 | O | H | Me | Me | Et | H | OMe | H | H |
| 7 | 0 | O | Me | Me | Me | Me | H | H | H | H |
| 8 | 1 | O | Me | Et | Et | Me | H | $NO_2$ | H | H |
| 9 | 1 | O | Me | Me | Me | Me | H | $CF_3$ | H | H |
| 10 | 2 | O | Me | 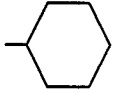 | 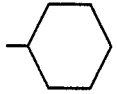 | Me | H | H | H | H |
| 11 | 2 | S | Me | Me | Me | Me | H | H | H | H |
| 12 | 1 | O | —CH$_2$CH=CH$_2$ | Me | Me | Me | Cl | Cl | H | H |
| 13 | 2 | O | —CH$_2$OH | Et | Et | Me | H | H | Me | H |
| 14 | 1 | S | 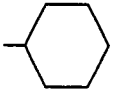 | Me | Me | Me | OMe | H | H | H |
| 15 | 1 | O | Me | —CH$_2$CH=CH$_2$ | —CH$_2$CH=CH$_2$ | Me | H | Me | H | H |
| 16 | 2 | S | Me | —CH$_2$CH$_2$OH | Me | Me | H | Cl | H | H |
| 17 | 1 | O | Me | Me | —CH$_2$CH$_2$OCH$_2$CH$_2$OCH$_3$ | Me | H | H | H | F |
| 18 | 1 | S | Me | —CH$_2$CH$_2$NMe$_2$ | —CH$_2$CH$_2$NMe$_2$ | Me | H | $CF_3$ | H | H |
| 19 | 1 | O | Me | —CH$_2$N(CH$_3$)CH$_2$Ph | Et | Me | H | H | H | CN |
| 20 | 1 | O | Me | 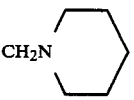 CH$_2$N | 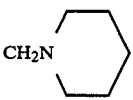 CH$_2$N | Me | H | H | H | H |
| 21 | 1 | NH | Me | Me | Me | Me | H | Cl | H | H |

(e) Dimethyl 4,6a,7,12-tetrahydro-4,6-dimethyl-4,7-methano-3a H-benzo[g]furo[2,3-d]-isoquinoline-6a,13β-dicarboxylate A solution of Compound 3d (0.80 mmol) in ethanol-free chloroform (8 mL) was added to a suspension of aluminum chloride (2.4 mmol) in ethanol-free chloroform (24 mL) at ambient temperature under nitrogen. After 4 hours, the reaction was quenched with dilute aqueous sodium bicarbonate (5 mL) and then extracted with methylene chloride (2×20 mL). The combined organic phases were washed with saturated aqueous sodium bicarbonate, brine and dried over anhydrous sodium sulfate.

It should be noted that for the preparation of Compounds 13 and 16 the hydroxyalkyl moiety is acylated with acetic anhydride prior to cyclization and then deacylated with sodium hydroxide.

EXAMPLES 22–39

Utilizing the general procedures of Examples 1, 2 or 3 and starting with appropriately substituted aryl aldehydes the following compounds of the formulae (I) and (II) wherein A is —CH=CH— and R is hydrogen are prepared.

| Compound | n | B | $R^1$ | $R^2$ | $R^3$ | $R^4$ | X | W | Z | U |
|---|---|---|---|---|---|---|---|---|---|---|
| 22 | 0 | O | Me | Et | Et | Me | H | H | H | H |
| 23 | 0 | S | Et | Et | Et | Et | H | H | H | H |
| 24 | 0 | O | H | Me | Me | Et | H | OMe | H | H |
| 25 | 0 | O | Me | Me | Me | Me | H | H | H | H |
| 26 | 1 | O | Me | Et | Et | Me | H | $NO_2$ | H | H |
| 27 | 1 | O | Me | Me | Me | Me | H | $CF_3$ | H | H |

-continued

| Compound | n | B  | R¹        | R²              | R³                   | R⁴ | X   | W   | Z  | U  |
|----------|---|----|-----------|-----------------|----------------------|-----|-----|-----|-----|-----|
| 28       | 2 | O  | Me        | 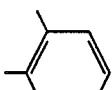 | 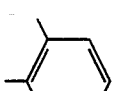 | Me  | H   | H   | H   | H   |
| 29       | 2 | S  | Me        | Me              | Me                   | Me  | H   | H   | H   | H   |
| 30       | 1 | O  | —CH₂CH=CH₂ | Me             | Me                   | Me  | Cl  | Cl  | H   | H   |
| 31       | 2 | O  | —CH₂OH    | Et              | Et                   | Me  | H   | H   | Me  | H   |
| 32       | 1 | S  | 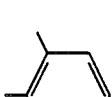 | Me   | Me                   | Me  | OMe | H   | H   | H   |
| 33       | 1 | O  | Me        | —CH₂CH=CH₂      | —CH₂CH=CH₂           | Me  | H   | Me  | H   | H   |
| 34       | 2 | S  | Me        | —CH₂CH₂OH       | Me                   | Me  | H   | Cl  | H   | H   |
| 35       | 1 | O  | Me        | Me              | —CH₂CH₂OCH₂CH₂OCH₃   | Me  | H   | H   | H   | F   |
| 36       | 1 | S  | Me        | —CH₂CH₂NMe₂     | —CH₂CH₂NMe₂          | Me  | H   | CF₃ | H   | H   |
| 37       | 1 | O  | Me        | —CH₂N(CH₃)(CH₂Ph) | Et                 | Me  | H   | H   | H   | CN  |
| 38       | 1 | O  | Me        | CH₂N-piperidinyl | CH₂N-piperidinyl    | Me  | H   | H   | H   | H   |
| 39       | 1 | NH | Et        | Et              | Et                   | Et  | H   | H   | Cl  | H   |

It should be noted that for the preparation of Compounds 31 and 34 the hydroxyalkyl moiety is acylated with acetic anhydride prior to cyclization and then deacylated with sodium hydroxide.

EXAMPLES 40–43

Utilizing the general procedures of Examples 1, 2 or 3 and starting with the appropriately substituted aryl aldehyde the following compounds of the formulas (I) and (II) wherein R is hydrogen are prepared.

EXAMPLE 44

As a specific embodiment of a composition of this invention an active ingredient, such as dimethyl 5,8-dihydro-4,6-dimethyl-4,8-methano-4H-thieno[2,3-a][4]benzazocine-7,13β-dicarboxylate is formulated to yield 5000 compressed tablets, each containing 50 mg of the active ingredient, as follows:

| Active ingredient | 250 grams |
|---|---|
| Starch | 70 grams |

| Compound | n | A | B | R¹ | R² | R³ | R⁴ | X | W | Z | U |
|----------|---|---|---|-----|-----|-----|-----|---|---|---|---|
| 40 | 0 | O | 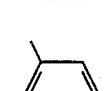 | Me | Me | Me | Me | H | OMe | H | H |
| 41 | 1 |   | NH | Et | Et | Et | Et | H | H | H | Cl |
| 42 | 2 |   | S  | Me | Me | Me | Me | H | CF₃ | H | H |
| 43 | 1 |   | NH | Et | Me | Me | Et | H | H | Me | H |

| -continued | |
|---|---|
| Dibasic calcium phosphate hydrous | 500 grams |
| Calcium stearate | 2.5 grams |

What is claimed is:

1. A compound represented by the following general structure formulae (I) or (II):

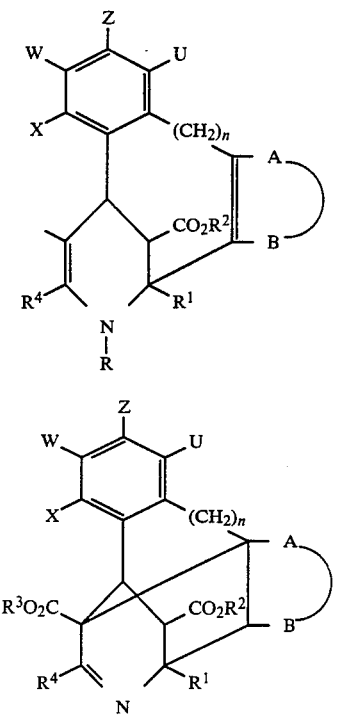

wherein:

n is 0 or 1;

A is oxygen or sulfur and B is —CH=CH—; or B is oxygen or sulfur and A is —CH=CH—; and R is hydrogen;

$R^1$ and $R^4$ independently are hydrogen or $C_1$–$C_8$ alkyl;

$R^2$ and $R^3$ independently are $C_1$–$C_8$ alkyl or $C_1$–$C_8$ aminoalkyl wherein the amino group is $NR^7R^8$ in which $R^7$ and $R^8$ independently are hydrogen, $C_1$–$C_8$ alkyl or $C_7$–$C_{14}$ phenylalkyl; and X, W, Z and U independently are hydrogen, $C_1$–$C_8$ alkoxy, $CF_3$, cyano, nitro or halo provided that at least two of X, W, Z and U are hydrogen.

2. A compound of claim 1 wherein: $R^1$, $R^2$, $R^3$ and $R^4$ are independently are $C_1$–$C_8$ alkyl; and X, W, Z, and U are hydrogen.

3. A compound of claim 2 which is dimethyl 5,8-dihydro-4,6-dimethyl-4,8-methano-4H-thieno[2,3-a][4]benzazocine-7,13β-dicarboxylate.

4. A compound of claim 2 which is dimethyl 3a,4-,6a,7-tetrahydro-4,6-dimethyl-4,8-methanoindeno [2,1-c]thieno[2,3-d]pyridine-6a,12β-dicarboxylate.

5. A compound of claim 2 which is dimethyl 5,8-dihydro-4,6-dimethyl-4,8-methano-4H-thieno[3,2-a][4]benzazocine-7,13β-dicarboxylate.

6. A compound of claim 1 which is dimethyl 4,6a,7,12-tetrahydro-4,6-dimethyl-4,7-methano-3aH-benzo[g]furo[2,3-d]isoquinoline-6a,13β-dicarboxylate.

7. A pharmaceutical composition, useful in the treatment of cardiovascular disorders in which a high cellular concentration of $Ca^{++}$ is a factor, comprising a nontoxic therapeutically effective amount of a compound according to claim 1 in an admixture with a pharmaceutically acceptable carrier.

8. A method of treatment for cardiovascular disorders in which a high cellular concentration of $Ca^{++}$ is a factor which comprises administering to a subject in need of such of such treatment a nontoxic therapeutically effective amount of a compound according to claim 1.

9. A process for the preparation of the compounds of claim 1 which comprises treating a compound of the following formula:

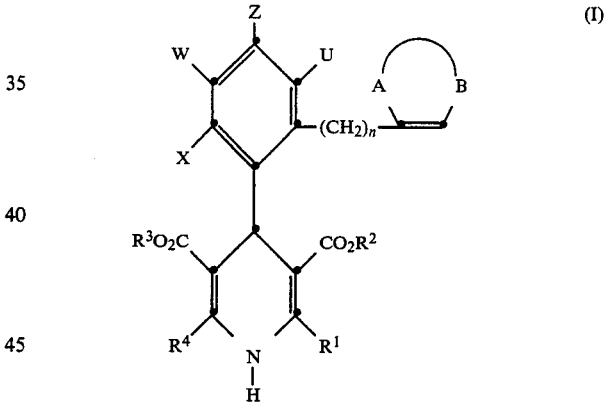

wherein n, A, B, $R^1$, $R^2$, $R^3$, $R^4$, X, W, Z and U are defined in claim 1 and R is hydrogen with Lewis acid in an inert solvent.

* * * * *